(12) United States Patent
Kjelleberg et al.

(10) Patent No.: US 7,026,353 B2
(45) Date of Patent: Apr. 11, 2006

(54) INHIBITION OF GRAM POSITIVE BACTERIA

(75) Inventors: Staffan Kjelleberg, La Perouse (AU); Peter David Steinberg, Marrickville (AU); Carola Holmstrom, Randwick (AU); Arthur Back, Randwick (AU)

(73) Assignee: Unisearch Limited, A.C.N., Sydney (AU)

( * ) Notice: Subject to any disclaimer, the term of this patent is extended or adjusted under 35 U.S.C. 154(b) by 0 days.

(21) Appl. No.: 10/434,193

(22) Filed: May 9, 2003

(65) Prior Publication Data
US 2004/0072898 A1    Apr. 15, 2004

Related U.S. Application Data

(63) Continuation of application No. 09/673,386, filed as application No. PCT/AU99/00284 on Apr. 16, 1999, now abandoned.

(30) Foreign Application Priority Data
Apr. 17, 1998  (AU) ...................... PP3034

(51) Int. Cl.
*A61K 7/06*  (2006.01)
*A61K 31/34* (2006.01)

(52) U.S. Cl. ..................... 514/473; 424/70.1
(58) Field of Classification Search ........... 514/473, 514/474; 549/295
See application file for complete search history.

(56) References Cited

U.S. PATENT DOCUMENTS 3,497,595 A    2/1970  Baker et al. ............... 424/269

FOREIGN PATENT DOCUMENTS

| WO | WO 96 01294 | 1/1996 |
| WO | WO 96 29392 | 9/1996 |
| WO | WO 99 54323 | 10/1999 |

OTHER PUBLICATIONS

Reichelt, J L et al. (1984) "Antimicrobial Activity from Marine Algae: Results of a Large-Scale Screening Programme." Hydrobiologia, Junk, The Hague, NL, 116/117: 158-168.

Manny, A J et al. (1997) "Reinvestigation of the Sulfuric Acid-Catalysed Cyclisation of Brominated 2-Alkyllevulinic Acids to 3-Alkyl-5-Methylene-2(5H)-Furanones." Tetrahedron, Elsevier Scientific Publishing, Amsterdam, NL, 53(46):15813-15826.

Chemical Abstracts 99: 200391 "Antimicrobial Constituents (of Marine Algae)", Ochi, Masamitsu, Suisangaku, Shiriizu (1983), 45 (Kaiso no. Seikagaku to Riyo), 101-19, Abstract only.

De Nys et al., (1995) "Broad Spectrum Effects of Secondary Matabolites From the Red Alga *Delisea pulchra* In Antifouling Assays", Biofouling, 8:259-271.

Kotsuki, Hiyoshizo et al., (1983) "Efficient Synthesis of Acetoxyfimbrolides and Beckerelides Analogs", Chemistry Letters, pp. 1007-1008 (The Chemical Society of Japan).

*Primary Examiner*—Rebecca Cook
(74) *Attorney, Agent, or Firm*—Morgan, Lewis & Bockius LLP

(57) ABSTRACT

A method of inhibiting the growth of a Gram positive bacterium, the method comprising treating the bacterium with an effective amount of one or more furanones having the Formula as set out in the Figure, wherein the effective amount of the one or more furanones does not substantially adversely effect the survival of an animal cell when exposed to the one or more furanones

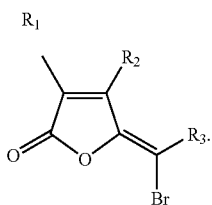

7 Claims, 4 Drawing Sheets

WHEREIN $R_1$ IS A HYDROGEN ATOM, A HYDROXYL, ESTER OR AN ETHER GROUP AND WHEREIN $R_2$ AND $R_3$ ARE EACH A HYDROGEN ATOM OR A HALOGEN ATOM.

INHIBITION OF GRAM POSITIVE BACTERIA

This is a continuation of application Ser. No. 09/673,386, filed Mar. 13, 2001 now abn, which is a PCT National Phase Application of PCT/AU99/00284 filed Apr. 16, 1999, which claims priority to Australian Application No. PP3034 filed Apr. 17, 1998. Each listed U.S. Patents and/or application is entirely incorporated herein by reference in its entirety.

TECHNICAL FIELD

The present invention relates to the use of furanone compounds as antibacterial agents, particularly as antibacterial agents for Gram positive bacteria.

BACKGROUND ART

It is known that a variety of furanone compounds possessing anti-fungal and antimicrobial properties can be isolated from red marine algae *Delisea fimbriata, Delisea elegans* and *Delisea pulchra* (Reichelt and Borowitzka (1984) Hydrobiologia 116: 158–168). When first isolated, it was thought that these compounds may be suitable as antimicrobial agents for use in animals including humans. Unfortunately, it was found that most if not all of these naturally occurring compounds were toxic to animal cells at the concentrations required to inhibit microorganisms and therefore unsuitable for many veterinary and medical applications.

Gram positive bacteria are a major problem in hospitals, on skin, in the dental area, for heart transplants, catheters, and other biomedical implants. Unfortunately, not all antimicrobial agents are active against Gram positive bacteria. Gram positive bacteria are also present in domestic areas like bathrooms, toilets and kitchens and can also cause a disease hazard for these sources. Accordingly, there is a need for more agents that are suitable to inhibit or kill these types of microorganisms in many varied situations including domestic, veterinary and medical applications.

The present inventors have now made the surprising finding that new synthetically produced furanone compounds have inhibitory activity against Gram positive bacteria without having corresponding deleterious activity against animal cells previously reported to be the case with naturally occurring furanones.

DISCLOSURE OF INVENTION

In a first aspect, the present invention consists in a method of inhibiting the growth of a Gram positive bacterium, the method comprising treating the bacterium with an effective amount of one or more furanones having the Formula as set out in FIG. 1, wherein the effective amount of the one or more furanones does not substantially adversely effect the survival of an animal cell when exposed to the one or more furanones.

In a preferred embodiment of the first aspect of the present invention, the furanone has the formula 2, 24, 25, 26, 27, 30, 33, 34, 45, mixtures and/or racemic mixtures thereof as shown in FIG. 2.

Preferably, the furanone is selected from is compound 2, 30, 45 or a mixture of compounds 33/34. More preferably, the furanone is a mixture of compounds 33/34 or compound 2.

Although compounds 33/34 have been found to be particularly suitable as antimicrobial agents, it will be appreciated, however, that other furanones may have similar or even greater activity against Gram positive bacteria. The finding by the present inventors that furanones other than the known naturally occurring compounds (for example compound 4) have activity against Gram positive bacteria without being substantially toxic to animal cells may lead to the production and use of other furanone compounds. Accordingly, it will be appreciated that the present invention covers other such compounds.

The present inventors have found that a concentration of a furanone of about 500 ng/ml was effective against a Gram positive bacterium. Higher concentrations were also effective but importantly were not toxic to animal cells. It will be appreciated that even lower concentrations may also be active against certain Gram positive bacteria and the present invention is not limited to the concentrations as tested and described herein.

The concentrations of furanones found to be active against Gram positive bacteria are not inhibitory against the Gram negative bacteria presently tested by the present inventors. The activity of the furanones are therefore surprisingly selective in their inhibitory action for Gram positive bacteria.

In a second aspect, the present invention consists in the use as an inhibitory agent against Gram positive bacteria of an effective amount of a furanone having the Formula as set out in FIG. 1, wherein the effective amount of the furanone do not substantially adversely effect the survival of an animal cell when exposed to the furanone.

In a preferred embodiment of the second aspect of the present invention, the furanone has the formula 2, 24, 25, 26, 27, 30, 33, 34, 45 mixtures and/or racemic mixtures thereof as shown in FIG. 2.

Preferably, the furanone is selected from is compound 2, 30, 45 or a mixture of compounds 33/34. More preferably, the furanone is a mixture of compounds 33/34 or compound 2.

The active furanones can be used as antibacterial agents for direct administration to mammals; as additives or preservatives for medical/surgical devices, disinfectants, soaps, shampoos, hand washes, denitrifies, household cleaning formulations, detergents for laundry and dishes; in wash and treatment solutions for topical use, instruments and devices including contact lenses, and other disinfecting and antibacterial applications The active furanones can be formulated as an antiseptic, disinfectant or antimicrobial agent. It will be appreciated that the formulations will be particularly useful in situations where it is necessary to inhibit or kill Gram positive bacteria without causing any deleterious effects on animal or mammalian cells.

In a third aspect, the present invention consist in a method of inhibiting the growth of a Gram positive bacterium in a subject infected with the bacterium, the method comprising administering to the subject an effective amount of one or more furanones having the Formula as set out in FIG. 1, wherein the effective amount of the one or more furanones do not substantially adversely effect cells of the subject.

In a preferred embodiment of the third aspect of the present invention, the furanone has the formula 2, 24, 25, 26, 27, 30, 33, 34, 45 mixtures and/or racemic mixtures thereof as shown in FIG. 2.

Preferably, the furanone is selected from is compound 2, 30, 45 or a mixture of compounds 33/34. More preferably, the furanone is a mixture of compounds 33/34 or compound 2.

In a fourth aspect, the present invention consists in a pharmaceutical composition active against Grain positive bacteria, the composition including one or more furanones having the Formula as set out in FIG. 1 together with one or more pharmaceutically acceptable diluents or excipients, wherein the one or more furanones do not substantially adversely effect animal cells at the inhibitory concentration used in the composition.

In a preferred embodiment of the fourth aspect of the present invention, the furanone has the formula 2, 24, 25, 26, 27, 30, 33, 34, 45 mixtures and/or racemic mixtures thereof as shown in FIG. 2.

Preferably, the furanone is selected from is compound 2, 30, 45 or a mixture of compounds 33/34. More preferably, the furanone is a mixture of compounds 33/34 or compound 2.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described in the following examples with reference to the accompanying drawings.

MODES FOR CARRYING OUT THE INVENTION

Methods and Results

Furanone Compounds

Figure 1:
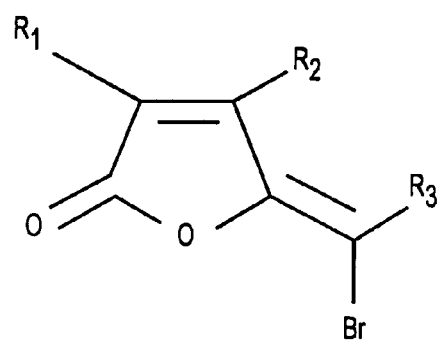
FIG. 1 shows the general structure of furanones suitable for the present invention wherein $R_1$ is a hydrogen atom, a hydroxyl, ester or an ether group and wherein $R_2$ and $R_3$ are each a hydrogen atom or a halogen atom.
Figure 2:
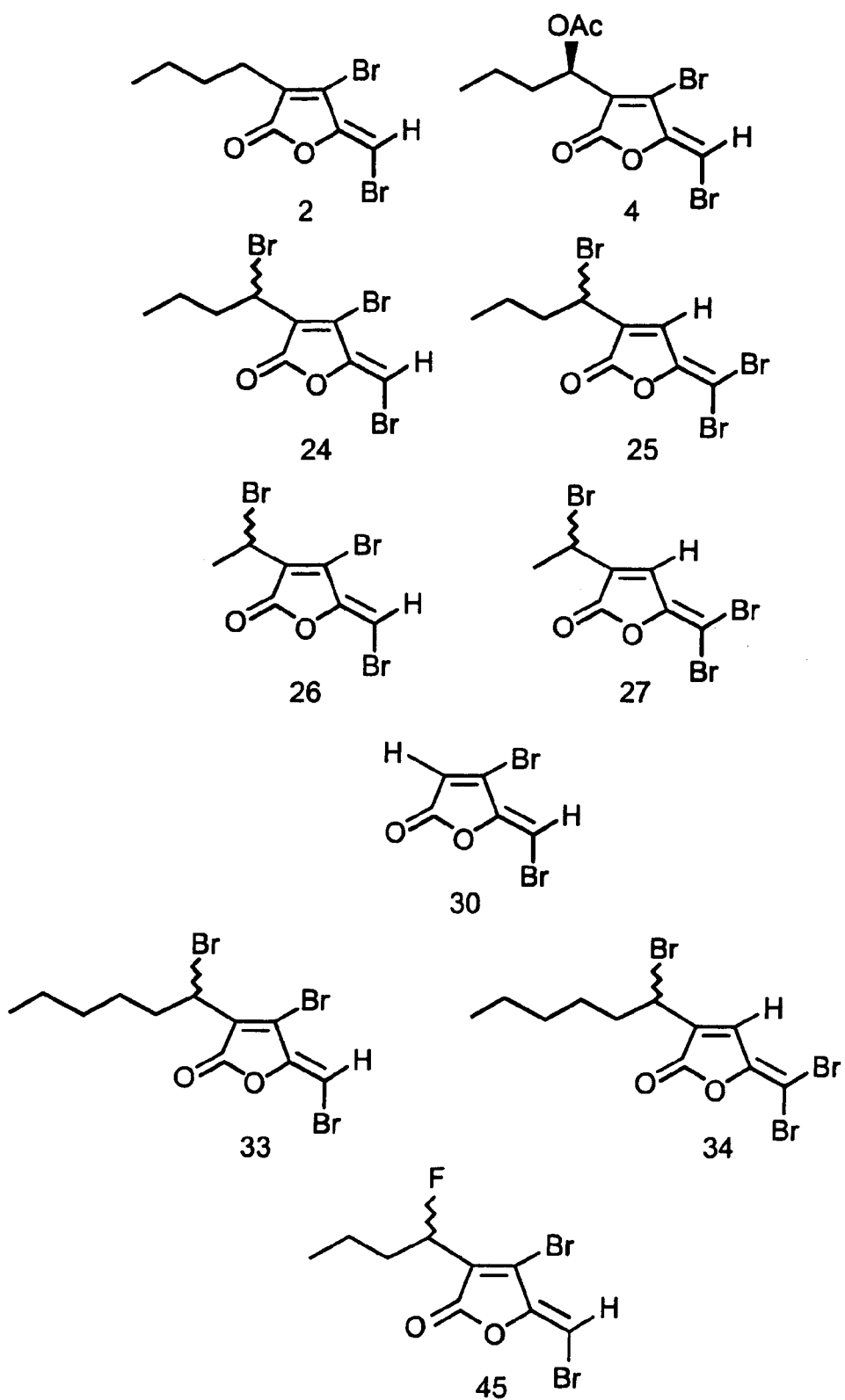
FIG. 2 shows the structure of furanone compounds formula 2, 24, 25, 26, 27, 30, 33, 34, 45 tested for activity against Gram positive bacteria.

A number of furanone compounds having structures shown in FIG. 2 were tested directly on Gram positive bacteria. Synthetically produced furanones are often produced as mixtures of isomers (e.g., 33/34, 26/27, etc.). It will be appreciated, however, that variations in these structures are similar enough to be expected to have an effect, and thus the present invention includes within its scope furanones with the more general structure shown in FIG. 1 which do not substantially adversely effect the survival of an animal cell when exposed to the furanone.

Microbiology

All initial screening of six different furanones against growth of *Staphylococcus aureus* and *Staphylococcus epidermidis* was performed in a BioRad 3550 Microplate Reader. Ten percent (10%) of an overnight culture ($10^8$ cells/ml, resulting in final cell densities of $10^6$ cells/ml) was added to the growth media. Nutrient Broth, containing furanones at the concentrations 10 and 1 µg/ml. The bacteria were incubated at 37° C. and growth was measured at 595 mm for 9 hours. Cytotoxicity in mammalian systems was measured as inhibition of the growth of mouse fibroblast cells.

The results showed several important features. First, the furanone compounds strongly inhibited growth at effective concentrations (e.g., 1 and 10 ug/ml) (comparable to that of standard commercial antibiotics. Second., synthetic, furanone compounds or mixtures of furanone compounds (e.g., 30; 24/25: 26/27: 33/34) were often more active than those furanone compounds which are produced naturally by the red algae *Delisea pulchra*, the main natural source of these fimbrolides. Third, a number of these furanone compounds were inhibitory at concentrations well below concentrations that inhibited moose fibroblasts. That is, the furanone compounds inhibited bacteria at non-toxic (to mammals) concentrations. For example, compounds 30 and 33/34 were the most active against both *Staphylococcus aureus* and *Staphylococcus epidermidis* (Table 1), completely inhibiting growth at 10 ug/ml. However, cultured mouse cells were not affected by compound 33/34 (for example) until 50 ug/ml.

TABLE 1

Activity of six different furanones against growth (after 9 hr) of two Gram positive bacteria and a mouse fibroblast cell line.

| Compound | *Staphylococcus aureus* | | *Staphylococcus epidermidis* | | Mouse cell line |
|---|---|---|---|---|---|
| | 10 µg/ml | 1 µg/ml | 10 µg/ml | 1 µg/mg | (µg/ml)[a] |
| *33/34 | 0 | 73.0[b] | 0 | 80.0 | 50 |
| *30 | 0 | 56.6 | 62.2 | 72.1 | 20 |
| *26/27 | 77.4 | 82.1 | 19.9 | 71.6 | 5 |
| *24/25 | 58.2 | 80.1 | 47.7 | 62.2 | 50 |
| #4 | 34.3 | 84.2 | 53.2 | 77.1 | 1 |
| #2 | 57.9 | 87.9 | 53.2 | 63.7 | 150 |

[a]Lowest concentration of furanones which significantly inhibited the growth of mouse fibroblast cell line L292. A 30% depression of growth is deemed significant
[b]% growth compared to the control value
*synthetically produced furanones
natural products The tests described above, while clearly demonstrating the efficacy of these compounds—particularly the synthetic furanones—against Gram positive bacteria, are unrealistic for many veterinary and medical applications in that they combine a very nutrient rich media with a very high initial inoculum density. In many clinical situations, colonising bacteria are much less dense initially, or will invade or contaminate much less nutrient rich media (e.g. saline). Thus a series of tests were done with a lower density innocula, or in less nutrient rich media. These experiments used compound 33/34, the most active synthetic mix in the initial screen.

Low numbers of overnight cells (*Staphylococcus aureus*) were inoculated to three different media; Nutrient broth (NB), and 10% and 5% of NB each diluted in 0.9% NaCl solution containing compound 33/34. This gave a final amount of 10 cells/ml media. The samples were incubated at 37° C. and growth was measured at 610 nm. Three different concentrations of compound 33/34 were tested, 500 ng/ml, 1 µg/ml and 5 µg/ml. Results reported are for 8 days (192 hr) and 19 days (456 hr) are shown in Table 2.

TABLE 2

Growth of *Staphylococcus aureus* (final amount of 10 cells/ml) in various media containing compound 33/34.

| | Concentration of compounds 33/34 | | |
|---|---|---|---|
| Medium | Control | 500 ng/ml | 1 µg/ml |
| Nutrient broth (NB) | 8 h[a] | growth after 30 hr | c |
| 10% NB[d] | 45 h | b | c |
| 5% NB[d] | 61 h | b | c |

[a]Time taken for control cultures to initiate growth
[b]No growth after 192 hr
[c]no growth after 456 hr
[d]NB media diluted with 0.9% NaCl solution Table 2 shows clearly that in these realistic growth conditions, concentrations of 33/34, as low as 500 ng/ml, completely inhibited the growth of *S. aureus*. These concentrations are two orders of magnitude less than those which affect mouse cell lines. The inhibitory concentrations are also lower than those used for any current commercial antibiotic against Gram positive bacteria.

Occular Applications

If has been reported that natural furanones have ability to inhibit the adhesion and swarming in a range of marine bacteria at concentrations that did not effect growth. In order to investigate whether different side chain would play any anti-bacteria roles, the effect of synthetic furanones (at lower concentrations) on growth of different ocular bacterial strains were examined.

Materials and Methods

Bacterial Strains

Bacterial strains included the commonly isolated ocular microorganism listed in Table 3.

TABLE 3

Ocular gram-positive bacteria used in the study

| Strain | Gram stain | Source |
|---|---|---|
| *S. aureus* 001 | Gram-positive cocci | Type strain |
| *S. aureus* 015 | Gram-positive cocci | Type strain |
| *S. aureus* 029 | Gram-positive cocci | CLPU |
| *S. epidermidis* 017 | Gram-positive cocci | CLARE |
| Corynebacterium 003 | Gram-positive rods | Infiltrative keratitis |

Furanone Compounds

Compounds 2, 24/25, 26, 30, 33/34 and 45 were examined for their effects of the growth of the bacterial strains. The concentrations used in the study for all the tested compounds were within the non-cytotoxic ranges.

Effect of Furanone Compounds on the Growth of Bacteria in TSB

Strains were cultured in 5 ml of TSB with or without SUs in 35° C. water bath with agitation (120 rpm). Growth rates were monitored by reading $OD_{660nm}$ at time intervals of 1, 2, 3, 4, 5, 7, and 24 hours.

Effect of Furanone Compounds on the Growth of Bacteria in Artificial Tear Fluid (AFT)

The formulation of ATF used in the study was reflected in the composition of closed-eye tears. It contained 2% (w/v) of human serum.

Overnight growing bacteria were harvested and washed once with PBS. After resuspending in ATF to $OD_{660}$ 0.1 ($10^8$ cells/ml), 200 µl of bacterial cell suspension was mixed with a same volume of ATF containing furanone compounds in a Bijio bottle. The final concentration of furanone compounds was 20 µg/ml. The cultures were then incubated at 35° C. for 24 h. Viable counts were quantified by plating out serial dilution of the ATF culture onto nutrient agar.

Minimum Inhibition Concentration of Furanone Compounds

One hundred µl/well of TSB containing two-fold serial diluted furanone compounds (at the concentration range from 20 to 1.25 µg/ml) were distributed in 96 well of microtitre plate. Ten µl of $10^4$ cells/ml overnight bacterial culture was added in each well to get the final concentration of cell numbers of $10^3$ cells/ml. After incubation for one or two days at 35° C., bacterial growth was measured at $Abs_{450nm}$ in a microtitre reader.

Results

Effect of Furanone Compounds on the Growth of Gram Positive Bacteria in TSB

Figure 3:
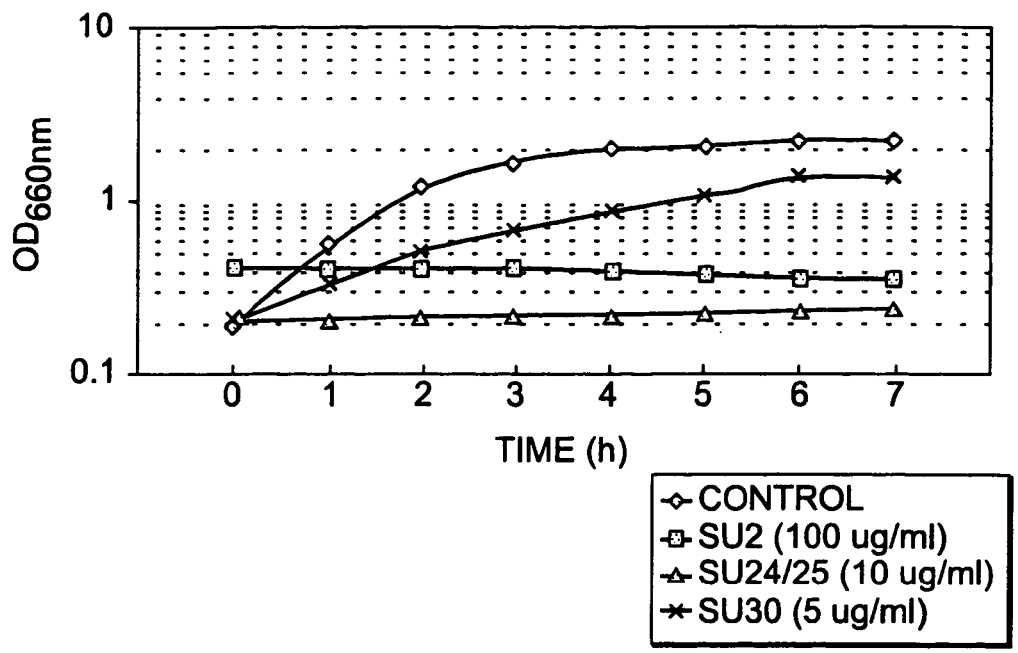
FIG. 3 shows the results of the effect of furanone compounds 2, 24/25 and 30 on the growth of *Staphylococcus aureus* 29.
Figure 4:
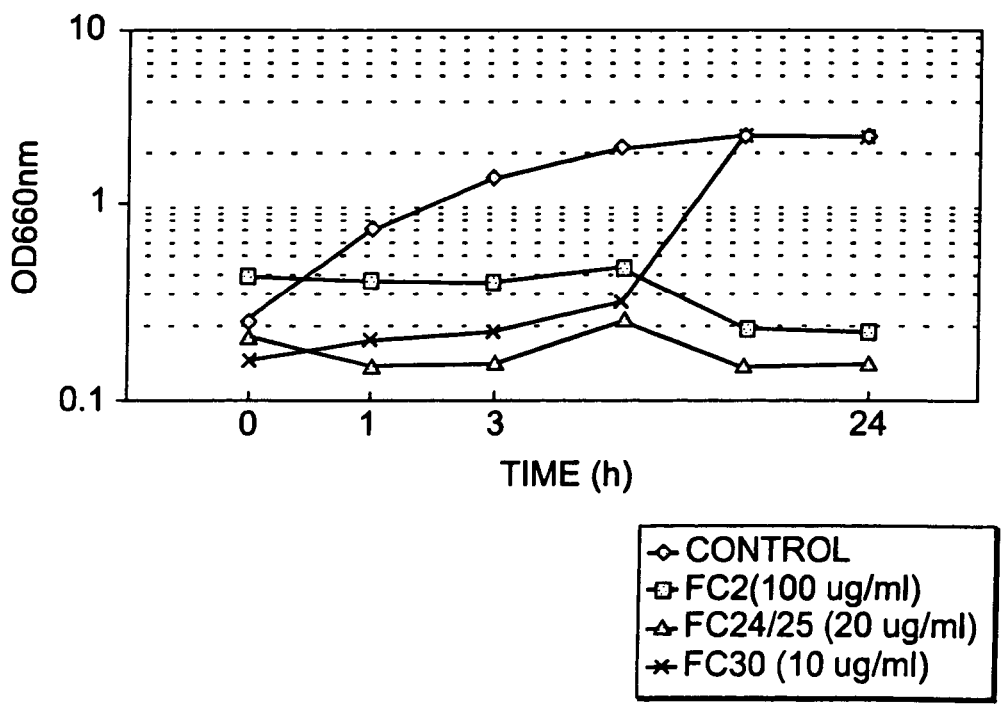
FIG. 4 is shows the results of the effect of furanone compounds 2, 24/25 and 30 on the growth of *S. aureus* 015.
Figure 5:
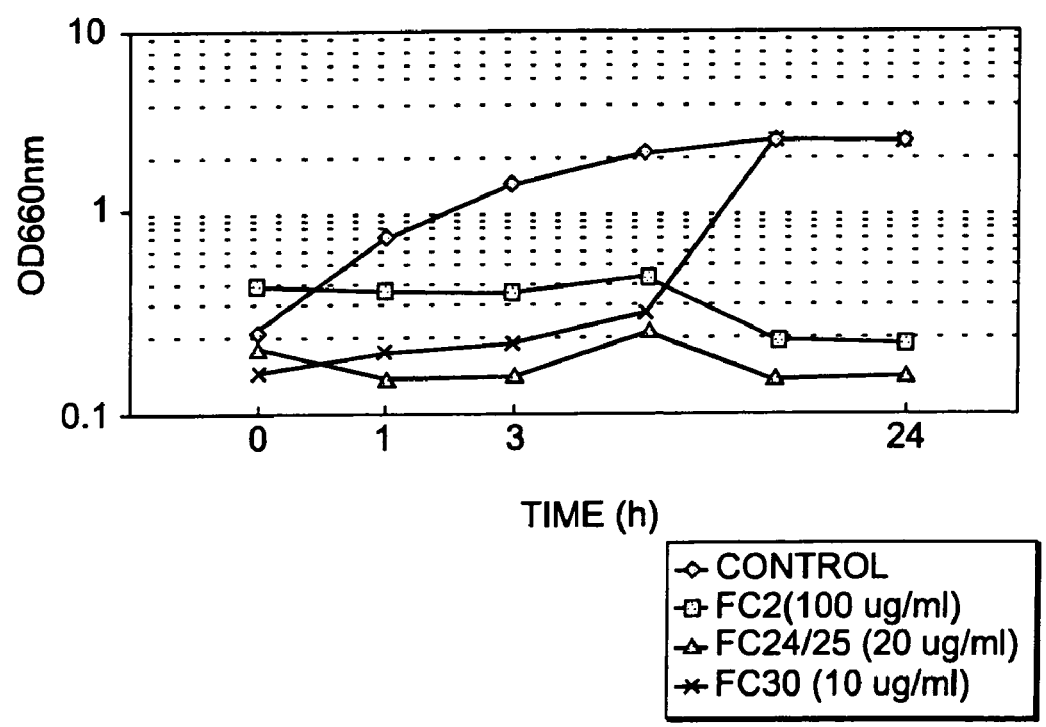
FIG. 5 is shows the results of the effect of furanone compounds 2, 24/25 and 30 on the growth of *S. epidermidis* 017.

The growth curves showed in FIGS. 3 to 5 demonstrated that furanone compound 2 and furanone compounds 24/25 inhibited the growth of *S. aureus* and *S. epidermidis* strains at the tested concentrations of 100 µg/ml and 20 µg/ml respectively; furanone compound 30 only slowed down the growth of *S. aureus* and *S. epidermidis* strains at lower concentrations (10 µg/ml. FIG. 5). There were only less than 8% growth of *S. aureus* strains after 24 h incubation time in the presence of furanone compounds 2 and 24/25 (Table 4). For Gram positive rods *Corynebacterium* sp 003, furanone compound 2 inhibited approximately 86% of growth at 100 µg/ml. Furanone compounds 24/25 (20 µg/ml) and 30 (10 µg/ml) only slowed down the growth of *Corynebacterium* sp 003 (Table 4), as the growth reached 71 and 90% in the presence of furanone compounds 24/25 (20 µg/ml) and 30 (20 µg/ml) respectively, after 24 h incubation.

TABLE 4

Percentage growth of Gram positive bacteria in the presence of furanone compounds compared to the control values (after 24 h).

| Strain | furanone compound 2 100 µg/ml | furanone compounds 24/25 20 µg/ml | furanone compound 30 10 µg/ml |
|---|---|---|---|
| G+ cocci: | | | |
| *S. aureus* 015 | 8 | 5 | 97 |
| *S. epidermidis* 017 | 7 | 3 | 91 |
| G+ rods: | | | |
| Corynebacterium 003 | 14 | 71 | 90 |

Low numbers of overnight cells (*Staphylococcus aureus*) were inoculated to 5% NB diluted in PBS (buffered NaCl solution) containing furanone compounds 33/34. This gave a final amount of 25 cells/ml media. The samples were incubated static at room temperature and growth was measured by CFU (colony forming unit). One concentration of furanone compounds 33/34 was tested, 5 µg/ml. Results reported are for 2 days, 5 days and 38 days and reported in Table 5.

TABLE 5

Growth of *Staphylococcus aureus* (final number of cells/ml) in 5% NB media containing furanone compounds 33/34.

| Time (days) | Control | Furanone compounds 33/34 (5 ug/ml) |
|---|---|---|
| 2 | $10^5$ cells/ml | no growth |
| 5 | $10^4$ cells/ml | no growth |
| 38 | $10^3$ cells/ml | no growth |

The results in Table 5 shows that growth of *S. aureus* was clearly inhibited at concentration 5 μg/ml.

A screening of six different furanone compounds against growth of *Staphylococcus aureus, Staphylococcus epidermidis. Streptococcus salivarius, Streptococcus pyogenes, Enterococcus faecalis* and *Micrococcus luteus* was performed in) a BioRad 3550 Microplate Reader. Ten percent of overnight cultures were added to the growth media. NB containing furanones at the concentration 10 μg/ml. The bacteria were incubated at 37° C. and growth was measured at 595 nm for 24 hours. The results are shown in Table 6.

TABLE 6

Activity of different furanone compounds (at concentration of 10 μg/ml) against growth (after 24 hr) of six Gram positive bacteria. Results given as % growth compared to the control value.

| Furanone Compound | Staph. aureus | Staph. epidermidis | Strep. salivarius | Strep pyogenes | Entero. faecalis | Micro. luteus |
|---|---|---|---|---|---|---|
| 45 | 4 | 22 | 69 | 26 | 85 | 100 |
| 33/34 | 0 | 0 | 0 | 0 | 62 | 63 |
| 30 | 0 | 62 | 73 | 50 | 54 | 86 |
| 26/27 | 77 | 20 | 92 | 84 | 75 | 85 |
| 24/25 | 58 | 48 | 87 | 72 | 92 | 65 |
| 4 | 34 | 53 | 85 | 0 | 75 | 75 |
| 3 | 22 | 32 | 86 | 14 | 89 | 75 |
| 2 | 58 | 53 | 86 | 87 | 77 | 86 |

Table 6 shows that all the different furanone compounds tested inhibit the growth of Gram positive bacteria and that the furanones act in a species specific manner. However, compound 33/34 demonstrated a broader range of inhibitory activity compared to the other compounds and also completely preveneds growth of four Gram positive bacteria.

DISCUSSION

Prior art (Reichelt and Borowitzka (1984) Hydrobiologia 116: 158–168) showed ail initial indication that naturally produced furanones can inhibit the growth of Gram positive bacteria at probably relatively high concentrations. However, the authors concluded that furanones were not useful as antibacterial agents in mammalian systems because they were toxic. The investigators based these conclusions primarily on tests with crude extracts of *Delisea pulchra* in which compound 4 is one of the more abundant furanones. The present inventors found compound 4 to be quite toxic against mammalian cell lines but determined that a number of other furanone compounds are necessarily toxic to mammalian cells.

Surprisingly, the present inventors have shown that the results with compound 4 are not generally representative of the effects of other furanone compounds, which are for the most part strongly inhibitory against Gram positive bacteria at non-cell line inhibitory concentrations. Moreover, synthetic furanone compounds tested were more effective than naturally occurring compounds.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of inhibiting the growth of a Gram positive bacterium, the method comprising treating the bacterium with an effective amount of one or more synthetically produced furanones having the following formula:

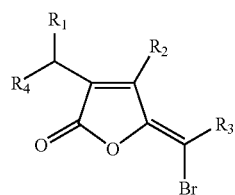

wherein $R_1$ is selected from the group consisting of a hydrogen atom, a halogen, a hydroxyl, an ester and an ether group, $R_2$ and $R_3$ are independently selected from a hydrogen atom or a halogen atom and $R_4$ is selected from the group consisting of C1, C3 and C5 alkyl, wherein the effective amount of the one or more synthetically produced furanones does not substantially adversely affect the survival of an animal cell when exposed to the one or more furanones.

2. A method of inhibiting the growth of a Gram positive bacterium, the method comprising treating the bacterium with an effective amount of one or more furanones having the structure selected from the group consisting of compounds of formula 24, 25, 26, 27, 30, 33, 34 and 45 or a mixture thereof:

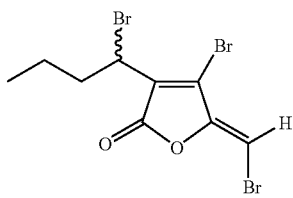

24

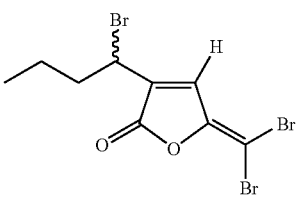

25

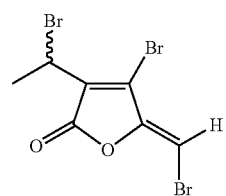

26

-continued

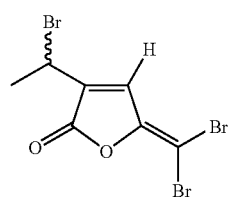
27

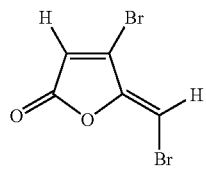
30

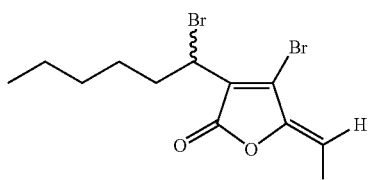
33

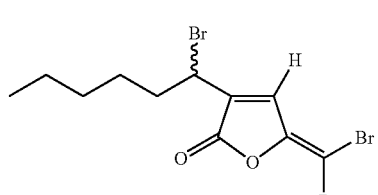
34

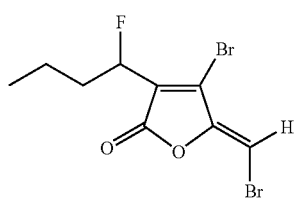
45 wherein the effective amount of the one or more furanones does not substantially adversely affect the survival of an animal cell when exposed to the one or more furanones.

3. The method according to claim 2 wherein the one or more furanones is the mixture of compounds 33 and 34.

4. The method according to claim 2 wherein the concentration of the one or more furanones is about 500 ng/nl.

5. A method of inhibiting the growth of a Gram positive bacterium in a subject infected with the bacterium, the method comprising administering to the subject an effective amount of one or more synthetically produced furanones having the following formula:

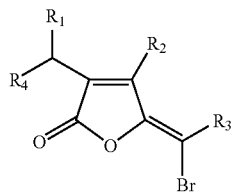

wherein $R_1$ is selected from the group consisting of a hydrogen atom, a halogen, a hydroxyl, an ester and an ether group, $R_2$ and $R_3$ are independently selected from a hydrogen atom or a halogen atom and $R_4$ is selected from the group consisting of C1, C3 and C5 alkyl, wherein the effective amount of the one or more synthetically produced furanones does not substantially adversely affect survival of cells of the subject when exposed to the one or more synthetically produced furanones.

6. A method of inhibiting the growth of a Gram positive bacterium in a subject infected with the bacterium, the method comprising administering to the subject an effective amount of one or more furanones having the structure selected from the group consisting of compounds of formula 24, 25, 26, 27, 30, 33, 34 and 45 or a mixture thereof;

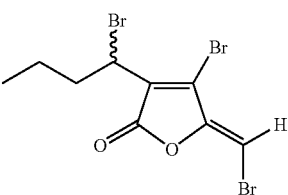
24

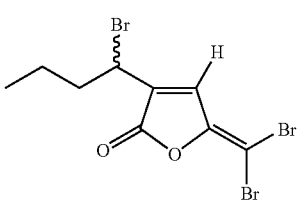
25

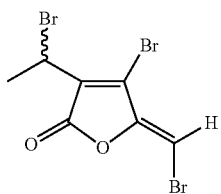
26

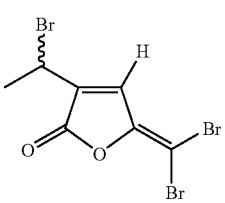
27

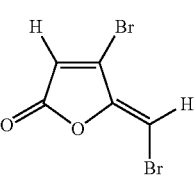
30

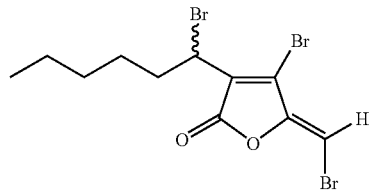
33
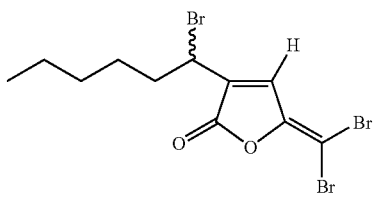
34
45
wherein the effective amount of the one or more furanones does not substantially adversely affect the survival of cells of the subject when exposed to the one or more furanones.
7. The method according to claim 6 wherein the one or more furanones is the mixture of compounds 33 and 34.
* * * * *